(12) United States Patent
Lee et al.

(10) Patent No.: US 6,723,507 B1
(45) Date of Patent: Apr. 20, 2004

(54) AMPLIFICATION OF DNA WITH A CONTROL SEQUENCE DIFFERING IN GC CONTENT

(75) Inventors: Martin A Lee, Salisbury (GB); Gale Brightwell, Salisbury (GB)

(73) Assignee: Her Majesty the Queen in right of Canada, as represented by the Secretary of State for Defence (CA)

( * ) Notice: Subject to any disclaimer, the term of this patent is extended or adjusted under 35 U.S.C. 154(b) by 0 days.

(21) Appl. No.: 09/786,446

(22) PCT Filed: Sep. 3, 1999

(86) PCT No.: PCT/GB99/02934

§ 371 (c)(1),
(2), (4) Date: Mar. 6, 2001

(87) PCT Pub. No.: WO00/14279

PCT Pub. Date: Mar. 16, 2000

(30) Foreign Application Priority Data

Sep. 7, 1998 (GB) .............................................. 9819418

(51) Int. Cl.$^7$ ............................ C12Q 1/68; C12P 19/34
(52) U.S. Cl. ......................................... 435/6; 435/91.2
(58) Field of Search ..................................... 435/6, 91.2

(56) References Cited

U.S. PATENT DOCUMENTS

| | | | |
|---|---|---|---|
| 5,559,013 A | * 9/1996 | Backus et al. | ............. 435/91.2 |
| 5,565,322 A | * 10/1996 | Heller | ............................ 435/6 |
| 5,691,146 A | 11/1997 | Mayrand | ...................... 435/6 |
| 5,705,366 A | * 1/1998 | Backus | ...................... 435/91.2 |
| 5,925,517 A | * 7/1999 | Tyagi et al. | ................... 435/6 |
| 6,174,670 B1 | * 1/2001 | Wittwer et al. | ................ 435/6 |

FOREIGN PATENT DOCUMENTS

| WO | WO97/46714 | 12/1997 |
|---|---|---|
| WO | WO98/36096 | 8/1998 |

OTHER PUBLICATIONS

Matthews et al., Analyt. Biochem. 169, 1–25 (1988).*

Lay and Wittwer: "Real–time fluorescence genotyping of factor v leiden during rapid–cycle PCR" Clin. Chem., vol. 43, No. 12, 1997, pp. 2262–2267.

Bernard et al.: "Integrated amplification and detection of the C677T point mutation in the methylenetetrahydrofolate reductase gene by fluorescence resonance energy transfer and probe melting curves" Anal. Biochem., vol. 255, Jan./ 1998, pp. 101–107.

Wittwer C T et al.: "Continuous fluorescence monitoring of rapid cycle DNA amplification" Biotechniques, US, Eaton Publishing, Natick, vol. 22, No. 1, Jan./ 1997, pp. 130–131.

Zimmermann K et al.: "Technical aspects of quantitative competitive PCR" Biotechniques, US, Eaton Publishing, Natick, vol. 21, No. 2, Aug./ 1996, pp. 268–270, 272–27.

Cantor: "Lighting up hybridization" Nature Biotechnology, US, Nature Publishing, vol. 14, 1996, p. 247.

Ririe et al, "Product Differentiation by Analysis of DNA Melting Curves During the Polymerase Chain Reaction", Analytical Biochemistry 1997, 245, 154–160.

* cited by examiner

Primary Examiner—Kenneth R. Horlick
(74) Attorney, Agent, or Firm—Nixon & Vanderhye, P.C.

(57) ABSTRACT

A method for amplifying a target DNA sequence, said method comprising amplifying said sequence in the presence of: a) a nucleic acid polymerase; b) at least one primer capable of hybridising to said target polynucleotide; c) an internal control sequence to which said primer is capable of hybridising and which is of similar length to the target DNA sequence but with a different percentage GC content; and d) label means for detecting the hybridisation of nucleic acids in the reaction; and detecting the hybridisation of the target and control sequences at different temperatures.

11 Claims, 8 Drawing Sheets

INTERNAL CONTROLS

——————  20%
                40%
                50%
                60% or
                80% GC

Fig. 8.
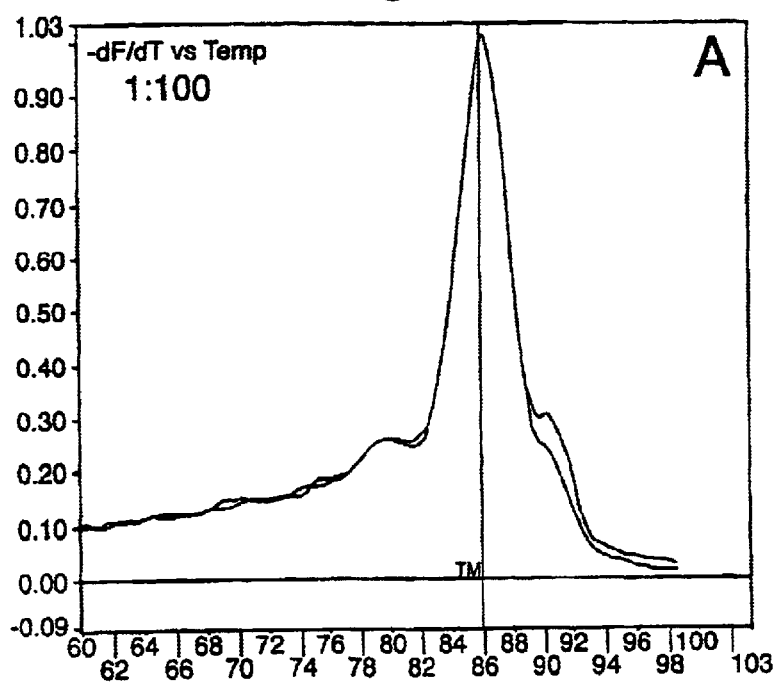
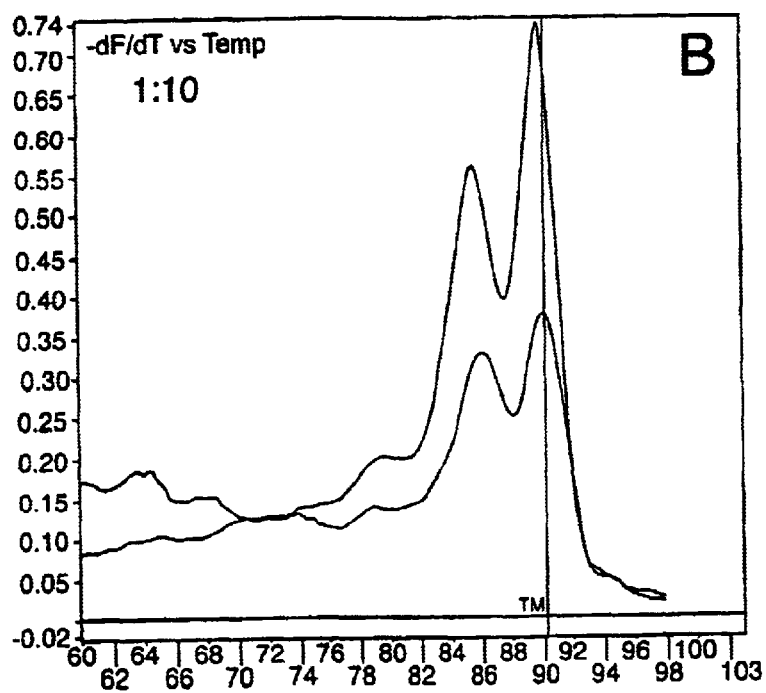

Fig.8(Cont.)
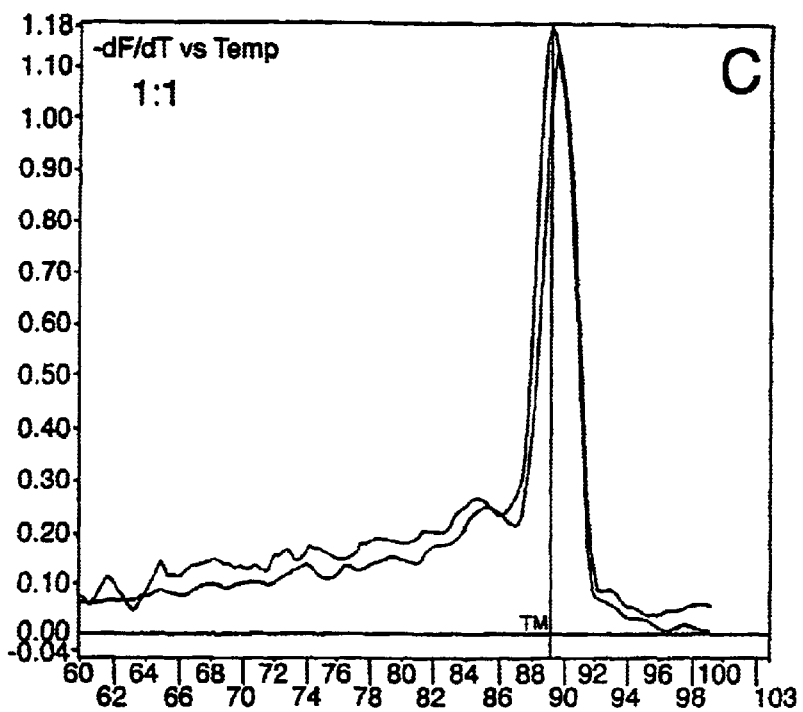
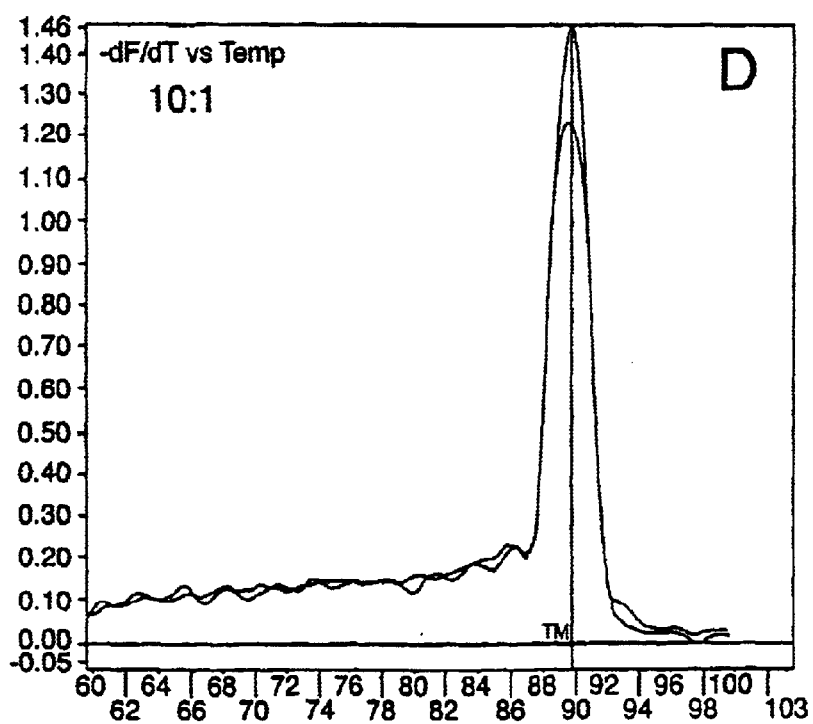

AMPLIFICATION OF DNA WITH A CONTROL SEQUENCE DIFFERING IN GC CONTENT

The present invention relates to a method of carrying out an amplification reaction and in particular a polymerase chain reaction (PCR) using an internal control mechanism.

Amplification reactions such as PCR reactions are well known and widely used. The PCR reaction procedure, in outline consists of the following steps, repeated cyclically.

Denaturation A mixture containing the PCR reagents (including the DNA to be copied, the individual nucleotide bases (A,T,G,C), suitable primers and polymerase enzyme) are heated to a predetermined temperature to separate the two strands of the target DNA.

Annealing: The mixture is then cooled to another predetermined temperature and the primers locate their complementary sequences on the DNA strands and bind to them.

Extension: The mixture is heated again to a further predetermined temperature. The polymerase enzyme (acting as a catalyst) joins the individual nucleotide bases to the end of the primer to form a new strand of DNA which is complementary to the sequence of the target DNA, the two strands being bound together.

A common problem in amplification reactions is establishing that the amplification has progressed adequately. In order to ensure that the amplification has progressed, it is common to include an "internal control" or standard sequence. This sequence is present in a known amount in the starting material and is designed such that it is amplified by the same primers as those used to amplify the target DNA sequence. The size of the amplified fragment however is different to that of the target DNA sequence. Hence, when the product is obtained, and analysed, for example using gel electrophoresis, the amplified control sequence produces a separate spot on the gel, and can indicate that the amplification reaction has progressed.

The problem with this method however is that because of the different size of the amplification target and the internal control sequence, they may be amplified with different efficiencies. Hence the degree of amplification of the control which has taken place will not be the same as that of the target sequence, which can give a misleading result in terms of the actual progress of the reaction.

The applicants have found an improved method for monitoring the progress of an amplification reaction, based upon the difference made to the hybridisation temperature of a sequence by the content of G and C bases present in the sequence.

The present invention provides a method for amplifying a target DNA sequence, said method comprising amplifying said sequence in the presence of (a) a nucleic acid polymerase (b) at least one primer capable of hybridising to said target polynucleotide, (c) a control sequence to which said primer is capable of hybridising and which is of similar length to the target DNA sequence but with a different percentage GC content, and (d) label means for detecting the hybridisation of nucleic acids in the reaction; and detecting the hybridisation of the target and control sequences at different temperatures.

Because the control sequence and the target sequence are of similar length, they will be amplified with similar amplification efficiencies. However, they will hybridise and denature at different temperatures, and so they will generate two discrete signals from the label means when they undergo denaturation in the course of the amplification reaction.

In general, the amplification will be effected in the presence of at least two primer sequences, a forward and reverse primer, which define each end of the sequences to be amplified, as is well known.

Suitable label means include are fluorescent labels. The signals can therefore be read using well known fluorescence monitoring devices.

Suitable fluorescent labels include intercalating dyes, which are interposed between the strands of a double stranded region of a DNA sequence. When the double stranded DNA region containing the intercalating dye reaches the predetermined temperature, it will be denatured, thus releasing the intercalating dye present between the strands. At this point the fluorescence from the mixture will reduce significantly, giving a readable signal.

The process using a double stranded DNA control sequence is illustrated diagrammatically in FIG. 1 hereinafter.

When intercalating dye (2) is added to a solution of double stranded DNA (1), it becomes interposed between the strands. The concentration of the dye (2) in this way produces a recognisable signal. On heating of the DNA so that it is denatured, dye is released and this event can be witnessed. Cooling to a temperature at which the said sequence will anneal again results in the intercalating dye becoming again trapped between the strands (see FIG. 1).

Suitable intercalating dyes include SYBRGreen™, SYBRGold™ and ethidium bromide or other commercially available dyes.

Alternatively, the fluorescent label used in the method of the invention may utilise fluorescence resonance transfer (FRET) as the basis of the signal. These labels utilise the transfer of energy between a reporter and a quencher molecule. The reporter molecule is excited with a specific wavelength of light for which it will normally exhibit a fluorescence emission wavelength. The quencher molecule is also excited at this wavelength such that it can accept the emission energy of the reporter molecule by resonance transfer when they are in close proximity (e.g. on the same, or a neighbouring molecule). The basis of FRET detection is to monitor the changes at reporter and quencher emission wavelengths.

For use in the context of the present invention, the control DNA sequence can be provided with a reporter and a quencher molecule, arranged so that the hybridisation of the strands alters the spatial relationship between the quencher and reporter molecules. Examples of such arrangements are illustrated in FIG. 2 and FIG. 3.

FIG. 2 illustrates an Example where the control sequence is a single stranded "hairpin" type sequence (3), where the end portions hybridise together. A reporter molecule (4) is attached in the region of either the 5' or the 3' end of the sequence and a quencher molecule (5) is attached at the opposite end such that they are brought into close proximity when the sequence is in the form of the loop. In this arrangement, FRET occurs and so fluorescent signal from the reporter molecule is reduced whilst the signal from the quencher (5) molecule is enhanced.

On denaturation however, the opposed end regions of the sequence separate so that the reporter and quencher molecules become spaced and so FRET no longer occurs. This changes the signals from the respective molecules and so this event can be detected.

Another arrangement is illustrated in FIG. 3. In this case, the reporter (4) and quencher molecules (5) are located on different strands (6, 7 respectively) of a DNA control sequence and are located such that on hybridisation of the strands, they are brought into close proximity to each other so that FRET can occur.

Yet a further embodiment is illustrated in FIG. 4. In this case, an intercalating dye (2) is used as an element of the FRET system. A quencher molecule (5) which can absorb radiation from the dye may be arranged on a strand of the control sequence such that it can absorb radiation from dye which is close proximity to on hybridisation of the strands. When the control sequence reaches a temperature at which it is denatured, the dye (2) is dispersed and so the signal from the quencher molecule (5) changes.

This embodiment is advantageous in that only a single label need be applied to the control sequence. Single labelled sequences of this type are more economical to produce.

In yet a further embodiment (FIG. 5), the reporter (4) and quencher (5) molecules are positioned on two oligonucleotide strands (9 and 10 respectively) which do not hybridise together. They are however designed so that in use, they hydridise to a DNA sequence present in the reaction mixture, which may be a plasmid (11), such that the reporter (4) and quencher (5) are brought into close proximity and FRET can occur between them, giving a recognisable signal.

The DNA sequence to which they bind may be part of the reaction system, for example where the reaction being monitored is a PCR reaction wherein the DNA sequence comprises or is part of the amplification target sequence. Alternatively, the sequences may be added to the reaction in order to provide the basis for the temperature probe of the invention.

The control sequence of the invention may be designed so that it denatures at any desired predetermined temperature depending upon the amount of the bases G and C contained therein. It is known that the bases C and G bind together more strongly than A and T. Therefore, the greater the higher the content of the bases G and C contained within a sequence, the higher the melting point of the sequence will be. This feature is illustrated in FIG. 6 which shows the melting temperature of a DNA sequence plotted against the percentage of and GC base pairs which are present within in. Thus, by adjusting the GC content, the control sequence of a predetermined length may be designed so that it denatures at a temperature which is remote from that of the amplicon.

This facilitates the overcoming of another problem which is known to occur with amplification reactions which include conventional internal control sequences. Frequently, the copy number or concentration of the sequences present has a significant impact on the efficiency of the amplification. If one of either the target or the internal control sequence is present in high copy number or concentration, it will be amplified preferentially and the other will not be seen. Using internal controls of the invention, the amplification conditions, in particular the denaturing temperature, can be adjusted so as to limit amplification of the dominant amplicon so both signals can be detected.

For example, where one of the target sequence or the internal control is going to be present in higher quantities in the reaction, the internal control may be designed such that the denaturation temperature of the lower concentration component, for example the control, is lower than that of the high concentration sequence which in this case would be the target sequence. If then during the amplification reaction, the denaturation conditions are adjusted such that the higher denaturation temperature (of the target sequence for example) is not reached, the internal control only will be amplified, at least for a limited number of cycles, so as to generate a distinguishable signal.

Thus in a preferred embodiment, the amplification reaction is effected under conditions which favour the amplification of the one of target sequence and under conditions which favour amplification of the internal control sequence. The denaturation temperature is the most convenient way of effecting this since by simply not allowing the mixture to reach the denaturation temperature of the higher melting component, the latter will not denature and so not hybridise with the primers and extend during the extension phase.

The method of the invention is particularly applicable for use in amplification reactions such as the polymerase chain reaction (PCR). In this case, the control sequence of the invention is introduced into the reaction vessel either separately to the target DNA sequence, or where appropriate, as part of the same plasmid.

BRIEF DESCRIPTION OF THE DRAWINGS

The invention will now be particularly described by way of example with reference to the accompanying diagrammatic drawings in which:

FIG. 8 illustrates the results of a PCR reactions carried out in the presence of internal controls for comparative purposes.

EXAMPLE 1

Figure 7:
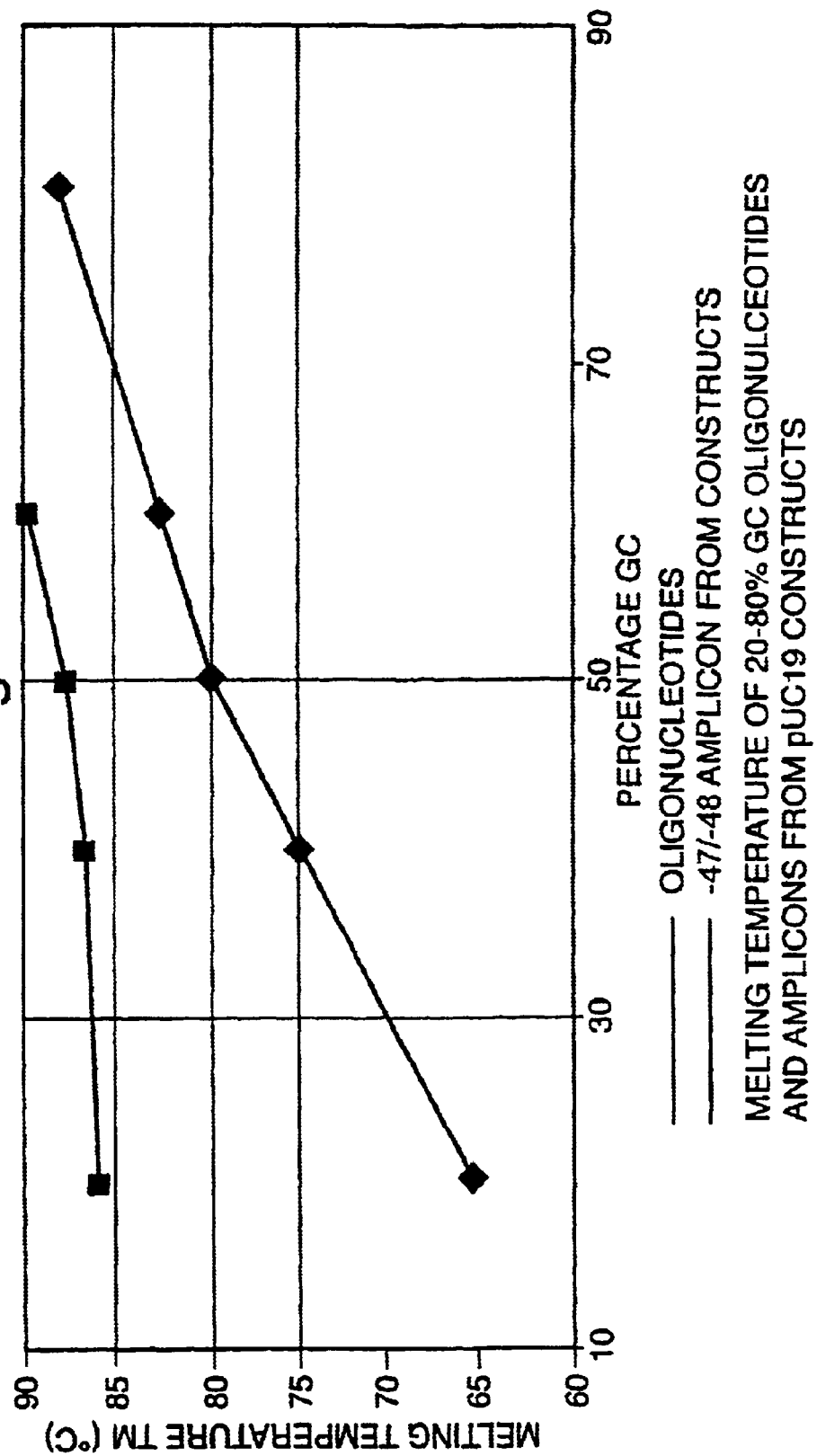
FIG. 7 shows the melting temperature of plasmid constructs and inserts as measured using the method of the invention, as a function of the percentage GC content of the construct, where the lighter line represents oligonucleotides and the darker line represents the −47/−48 amplicon from constructs.
Figure 9A:
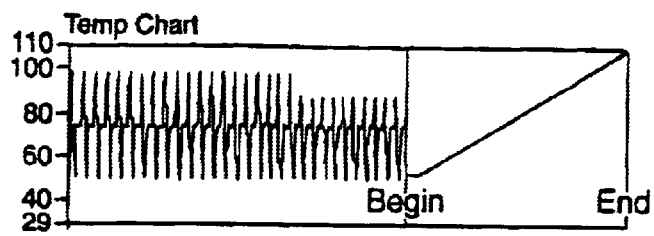
FIGS. 9A–9F show the results of similar PCR reactions carried out at selected temperatures in accordance with the invention.
Figure 9B:
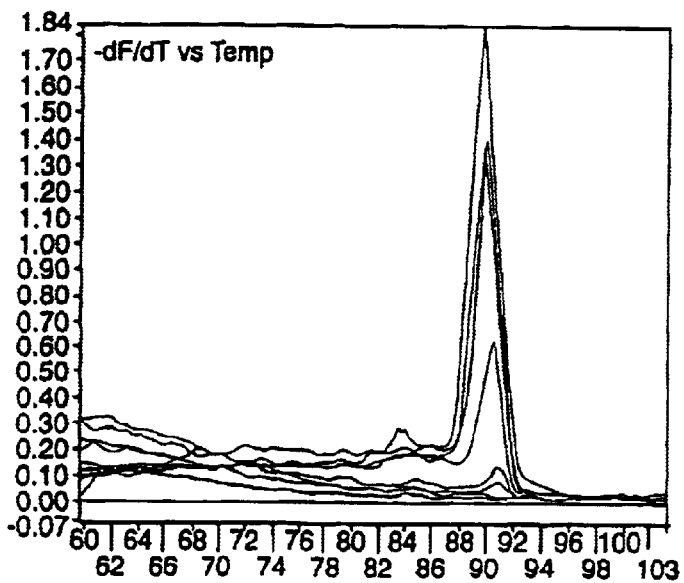
Figure 9C:
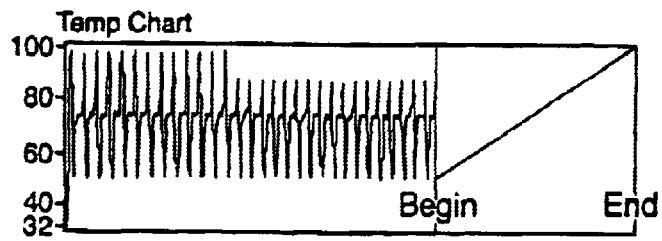
Figure 9D:
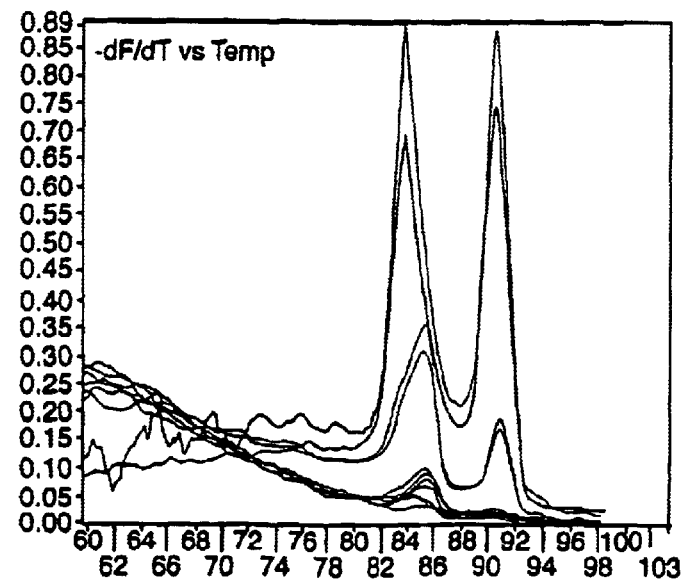
Figure 9E:
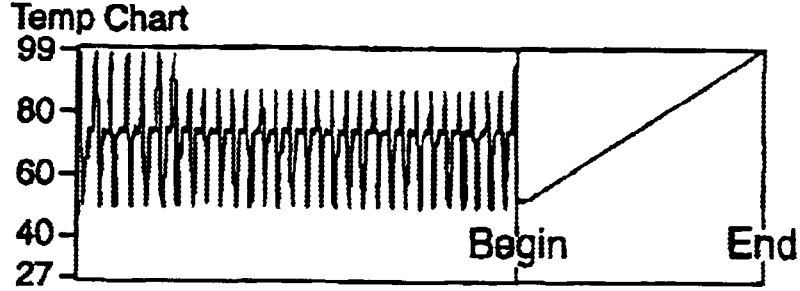
Figure 9F:
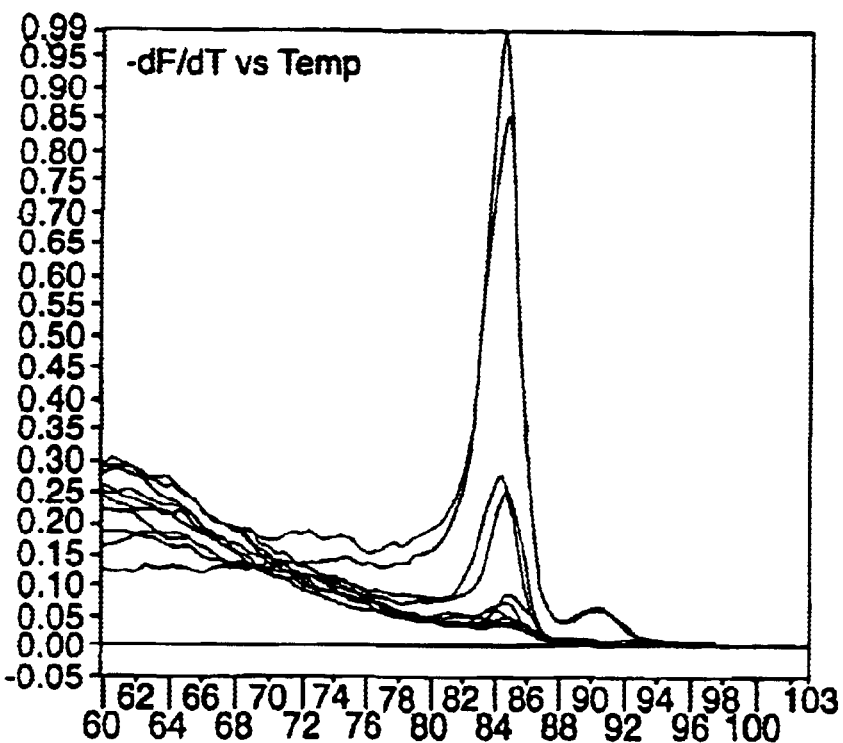

Oligonucleotides, 60 base pairs in length, were designed by randomly removing the letters G, A, T and C from a paper bag. Complementary pairs of the thus formed oligonucleotides were mixed together at a final concentration of 1 μM and 1:40,000 dilution of SYBRGreen™ reference dye. The mixtures were then loaded into LightCycler™ tubes and the temperature slowly raised from 40° C. to 110° C. The fluorescence at 520 nm was measured and was seen to drop off as the temperature was raised. The differential of fluorescence was used to determine the peak rate of change (i.e. drop) which corresponds to the strands melting. 20%, 40%, 50% 60% and 80% GC oligos were used in different experiments. The results, expressed as a graph of melting temperature vs GC content is shown as FIG. 7.

EXAMPLE 2

Figure 1:
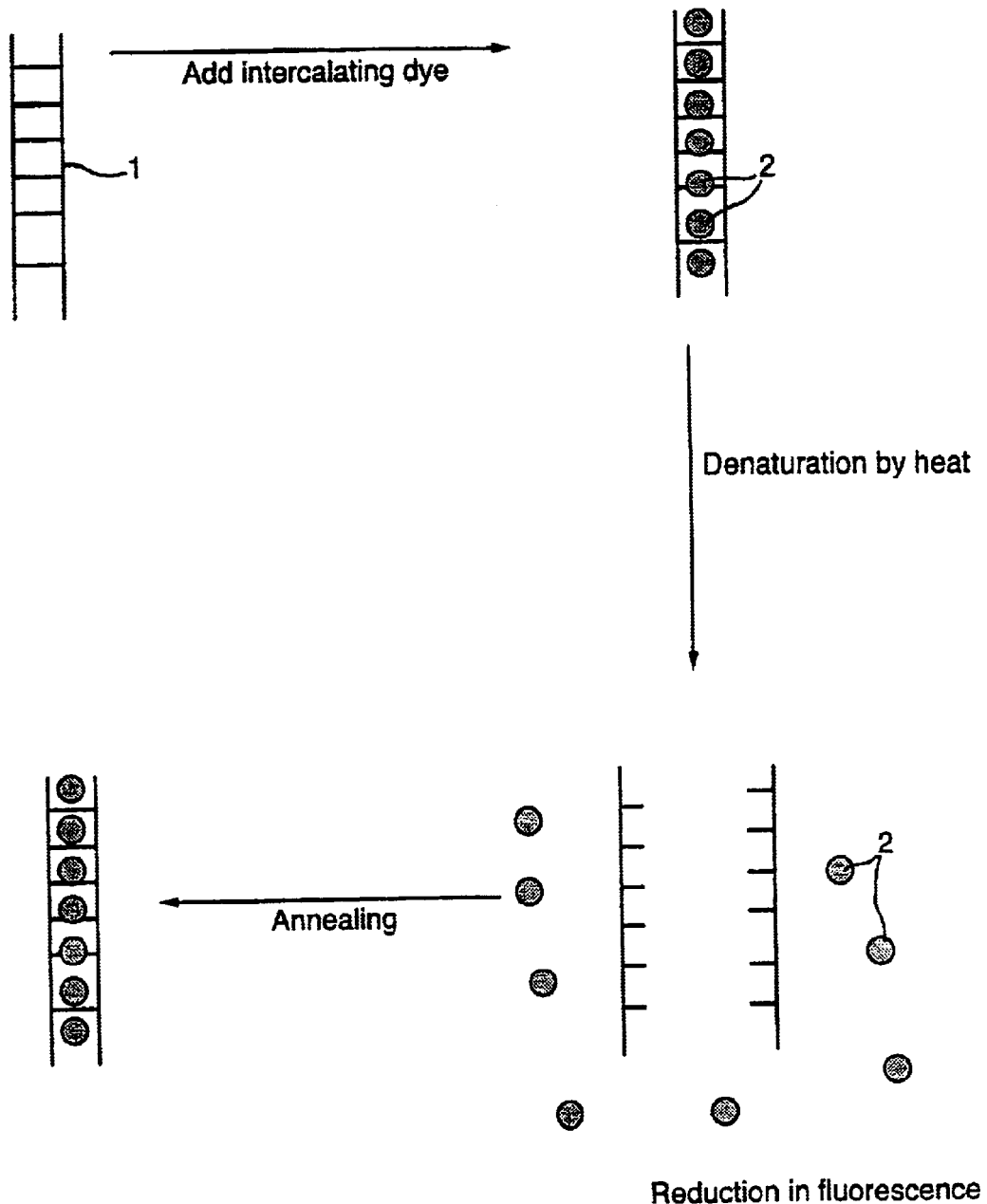
FIG. 1 illustrates the formation and use of a labelled control sequence in the method of the invention.
Figure 2:
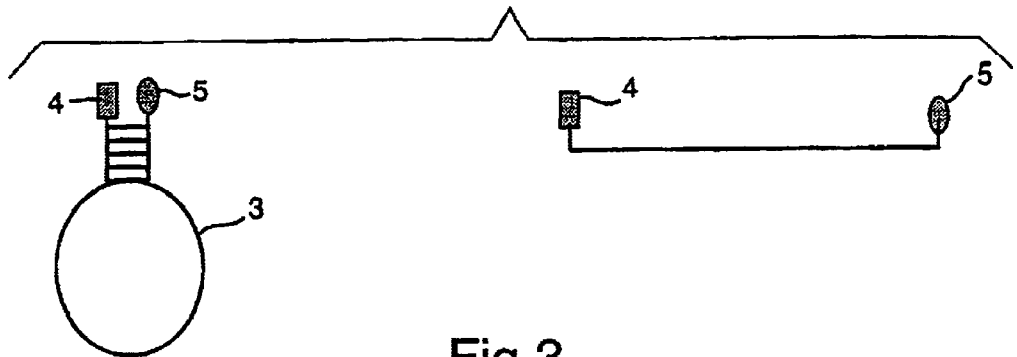
FIGS. 2 to 5 represent alternative embodiments of the labelled control sequences of the invention and the denaturation thereof.
Figure 3:
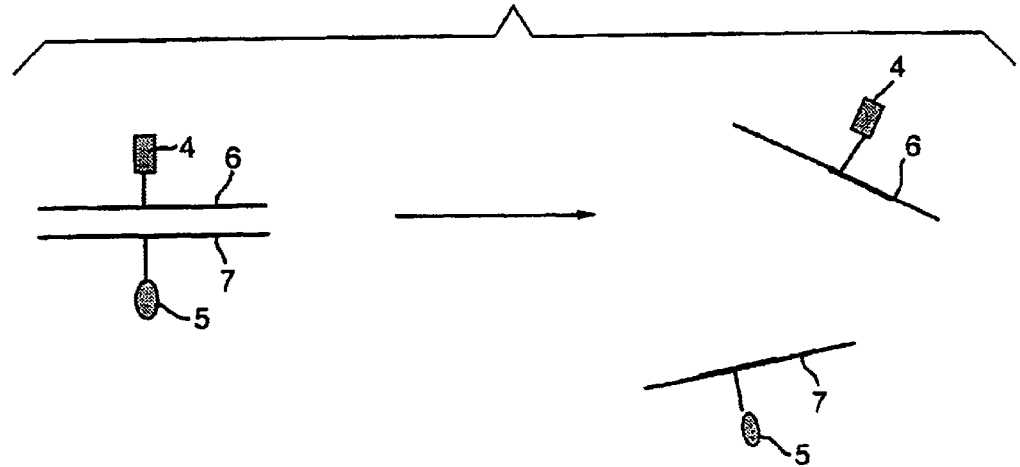
Figure 4:
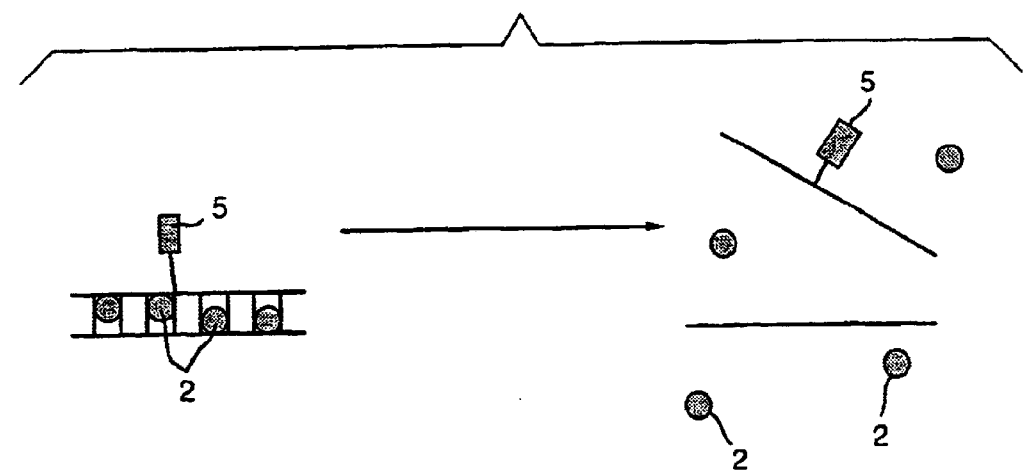
Figure 5:
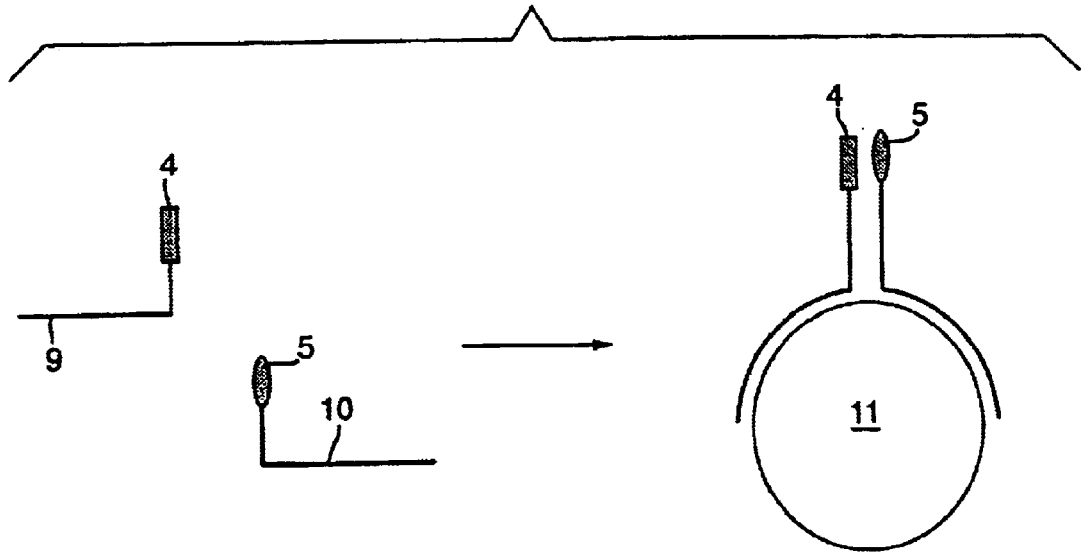
Figure 6:
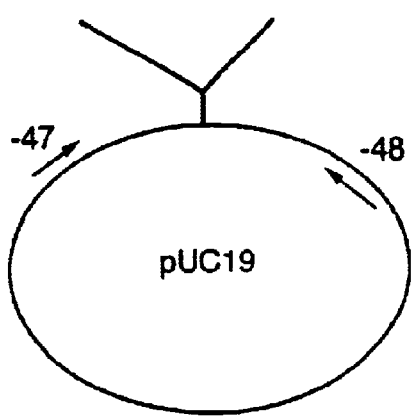
FIG. 6 illustrates a construct used as an internal control in accordance with the invention.

The different GC duplexes used in Example 1 were cloned into the vector polylinker of pUC19 plasmid as illustrated in FIG. 6. This plasmid was subjected to a polymerase chain reaction using vector primer sites, the −47 and −48 sequencing primer sites as follows:

A PCR master mix cocktail was made that contained:
Bio/Gene 2× LightCycler Master Mix 3 mM Mg++ (Bio/Gene UK LTD)200 μl
SYBRGold Reference dye (Molecular Probes) 1:20,000 dilution 20 μl -47 pUC primer 10 uM 40 µl
-48 pUC primer 10 uM 40 µl
Water 60 µl This master mix cocktail was thoroughly mixed before 72 µl aliquots were placed into 5 tubes, A, B, C, D and one tube marked −ve. To the −ve tube 8 µl of water was added and the contents of this tube were used a −ve controls. To the other tube 8 µl of differing samples were added so that in the final mix the tubes had the following amount of each construct.

| Tube | 60% GC Construct | pUC 19 |
|------|------------------|--------|
| A    | 1                | 100    |
| B    | 1                | 10     |
| C    | 1                | 1      |
| D    | 10               | 1      |

10 µl were load into LightCyler™ tubes (Idaho Technology) and thermal cycled at

95° C. −1 s
50° C. −1 s
74° C. −10 s
×40 Cycles

Then the products were melted by slowly raising the temperature from 40° C. to 95 at 0.1° C. per second whilst monitoring Fluorescence at 520 nM.

The results are shown in FIG. 8. pUC 19 produces a product with a melt profile at 85° C. whilst the internal control product is at 90° C. The figure shows how copy number of each construct at the start of the reaction affects the yield of each amplicon. If one construct is in excess this will be amplified preferentially and the other target can not be detected.

The PCR described above was repeated using the same constructs but with different thermal profiles. The results are shown FIG. 9. The thermal profile used in each case is shown at the top of the figure. The results show that by reducing the denaturing temperature of the PCR, the yield of product from each construct can be controlled. The melting temperature of the internal control is 90° C., by reducing the denaturing temperature to 85° C. the amount of ssDNA of the control product is reduced in the denaturing and extension steps, thus limiting its amplification. Two clear signals can then be observed.

This is useful because modification of the thermal profile will allow the internal control to be selectively amplified over a range of specific target concentrations.

What is claimed is:

1. A method for amplifying a target DNA sequence, said method comprising
   (i) amplifying said sequence in the presence of
      (a) a nucleic acid polymerase,
      (b) at least one primer capable of hybridizing to said target DNA sequence,
      (c) a control sequence to which said primer is capable of hybridizing and which is of a similar length to the target DNA sequence but with a different percentage GC content and
      (d) label means for detecting hybridization of one or more of:
         1—the primer to either of the target sequence and control sequence
         2—the target sequence to a complement of the target sequence; and
         3—the control sequence to a complement of the control sequence;
      said amplifying comprising at least one hybridizing step and at least one denaturation step; and
   (ii) detecting hybridization of the target and control sequences at different temperatures; wherein the conditions used in the amplification are such that amplification of one of either the target sequence or the control sequence is favoured, said conditions favouring amplification of the sequence which is present in smaller amounts wherein the temperature of the denaturation step of the amplification is controlled such that the sequence which is present in smaller amounts is denatured in preference to the other sequence, and the control sequence is designed such that the temperature of denaturation of the control sequence is lower than the temperature of denaturation of the target sequence when the control sequence is present in smaller amounts, and the temperature of denaturation of the control sequence is greater than the temperature of denaturation of the target sequence when the target sequence is present in smaller amounts.

2. A method according to claim 1 wherein at least a forward primer and a reverse primer are used to amplify both the target nucleotide sequence and the control sequence.

3. A method according to claim 1 or claim 2 wherein the label means comprises a fluorescent label.

4. A method according to claim 3 wherein the label means comprises an intercalating dye.

5. A method according to claim 4 wherein the intercalating dye is SYBRGreen™, SYBRGold™ or ethidium bromide.

6. A method according to claim 3 wherein the fluorescent label utilises fluorescence resonance transfer (FRET) as the basis of the signal.

7. A method according to claim 6 wherein the control DNA sequence is provided with a reporter and a quencher molecule arranged so that formation of a duplex by the control sequence alters the spatial relationship between the quencher and reporter molecules.

8. A method according to claim 7 wherein the control sequence is a single stranded sequence, where the end portions hybridise together, and in which the reporter molecule is attached in the region of either the 5' or the 3' end of the sequence and the quencher molecule is attached at the opposite end.

9. A method according to claim 7 wherein the reporter and quencher molecules are located on opposite strands of a double stranded DNA control sequence and are located such that on hybridisation of the strands, they are brought into close proximity to each other so that FRET can occur.

10. A method according to claim 6 wherein the label means comprises an intercalating dye and quencher molecule, provided on the control sequence, which can absorb radiation from the dye when in the form of a double stranded molecule.

11. A method according to claim 6 in which a reporter molecule is provided on a first oligonucleotide strand and a quencher molecule is provided on a second oligonucleotide strand, said first and second strands being off similar length to the target DNA sequence and having a similar GC content to each other, said first and second strands being hybrisable to a third DNA sequence present in the reaction mixture such that on hybridisation, the reporter and quencher molecules are brought into close proximity to each other.

* * * * *